United States Patent [19]

Bauser et al.

[11] Patent Number: 4,840,636
[45] Date of Patent: Jun. 20, 1989

[54] MODIFYING THE SURFACE OF THE INTERIOR PORE WALLS OF OBJECTS SUCH AS MEMBRANES WITH GAS ACTIVATED BY PARTIAL BRUSH DISCHARGE

[75] Inventors: Herbert Bauser; Bernd Schindler, both of Stuttgart; Horst Chmiel, Leonberg, all of Fed. Rep. of Germany

[73] Assignee: Fraunhofer Geselschaft E.V., Munich, Fed. Rep. of Germany

[21] Appl. No.: 658,762

[22] Filed: Oct. 9, 1984

[30] Foreign Application Priority Data

Oct. 18, 1983 [DE] Fed. Rep. of Germany ....... 3337763

[51] Int. Cl.$^4$ .................... B01D 13/04; B01D 39/14; C08J 9/36
[52] U.S. Cl. .................. 8/115.52; 8/115.68; 8/149.2; 68/5 R
[58] Field of Search .......... 8/115.52, 115.68

[56] References Cited

U.S. PATENT DOCUMENTS

| 3,188,165 | 6/1965 | Magat et al. | 8/115.52 |
| 3,188,228 | 6/1965 | Magat et al. | 8/115.52 |
| 3,650,669 | 3/1972 | Osborn et al. | 8/115.52 |
| 3,817,701 | 6/1974 | Thorsen | 8/115.52 |
| 4,104,807 | 8/1978 | Braun | 34/5 |
| 4,163,714 | 8/1979 | Gregor | 210/639 |

FOREIGN PATENT DOCUMENTS 3106188 8/1982 Fed. Rep. of Germany.
59-025989 2/1984 Japan.

Primary Examiner—A. Lionel Clingman
Attorney, Agent, or Firm—Ralf H. Siegemund

[57] ABSTRACT

A stream of gas is forced through the pores of an object and either the gas itself or a component thereof is electrically activated through partial brush discharge such that reaction products will modify the surface of the pore walls as the gas flows through. The method avoids vacuum deposition methods as well as wet-coating methods and is applicable for either hydrophobizing or hydrophilizing objects and for improving, for example, biochemical activities or compatability of the object with a liquid to be filtered later.

14 Claims, 2 Drawing Sheets

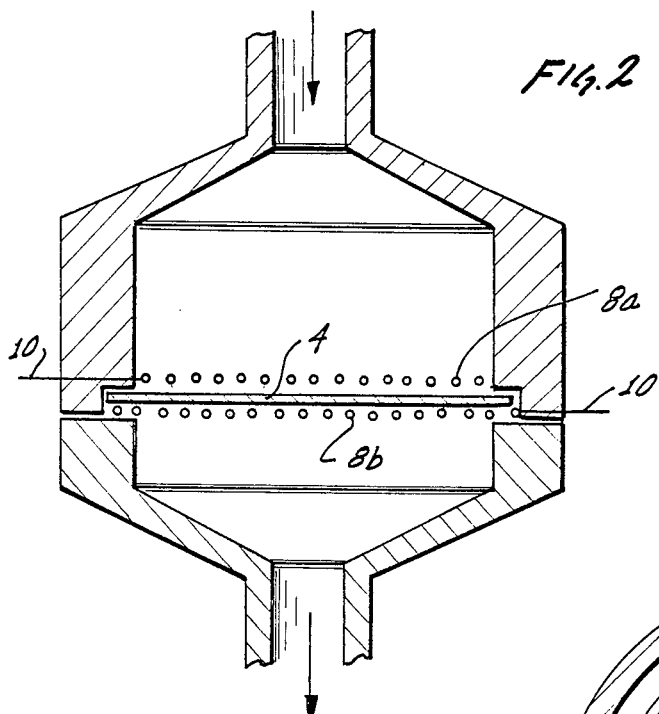
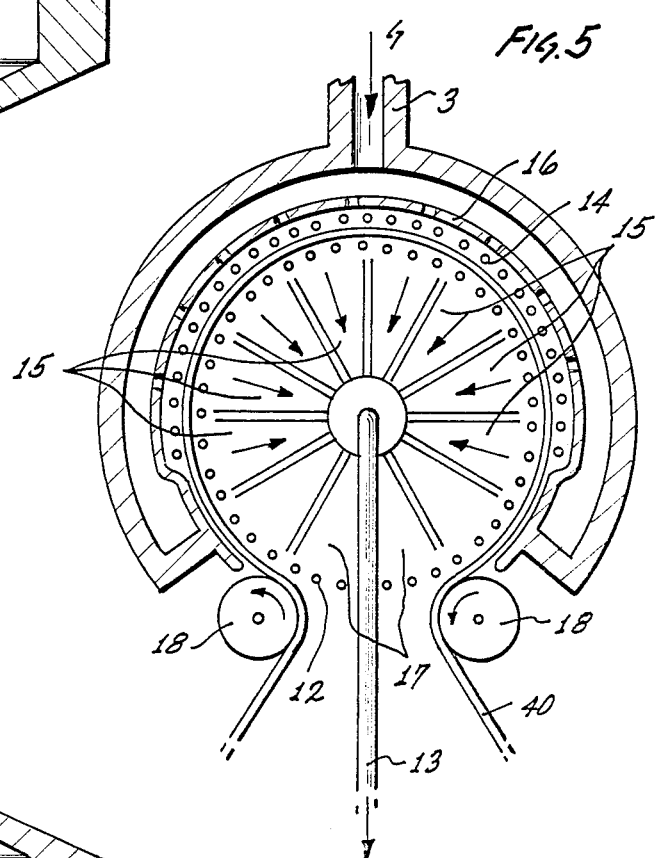
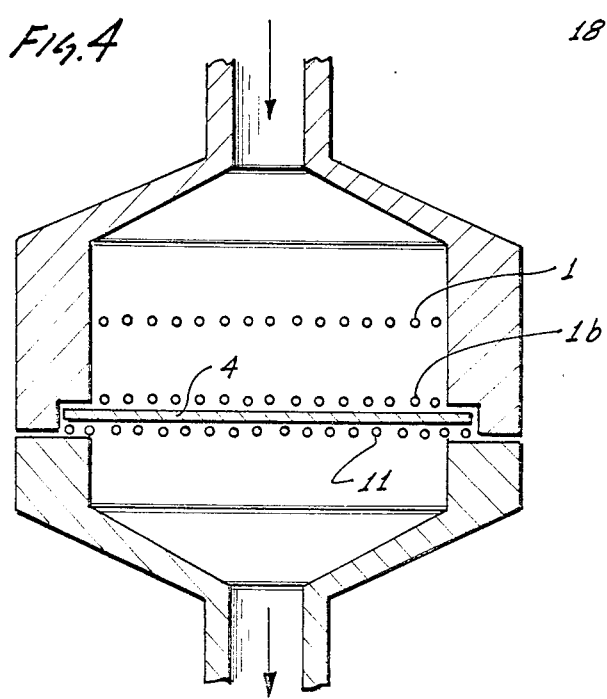

MODIFYING THE SURFACE OF THE INTERIOR PORE WALLS OF OBJECTS SUCH AS MEMBRANES WITH GAS ACTIVATED BY PARTIAL BRUSH DISCHARGE

BACKGROUND OF THE INVENTION

The present invention relates to modifying the surface of the inner walls of pores in objects such as membranes to be used for separating material or phases of matter, preferably for filtering biological liquids or liquids containing organic molecules under further utilization of an activator which traverses the pores. Membrane materials in relation to which the invention can be practiced include for example polysulfone, polycarbonate, polypropylene, polyethylene, polyamid, polyurethane, cellulose, senorized hydrocarbons such as polytetrafluoroethylene (see Pusch and Walch in Angew. Chem. 94 (1982 670-695).

Membranes made of synthetic material or of regenerated natural material are used for example for filtering biological liquids or other liquids containing organic molecules in general. Solutions in question are for example protein solutions such as whey, waste liquid which arises in the process of paper making, sugar refining or gelatin manufacture; still other liquids are oil emulsions, etc. In all these instances, the problem arises that through the adsorption of organic molecules such as proteins, on the surface of the membrane, i.e., the inner walls of pores therein, the cross-section of flow is in effect reduced so that the throughput or throughflow of matter through the membrane is diminished and the efficiency of operation is reduced accordingly.

Known membranes exhibit a further problem, namely the curious property that most synthetic membranes are hydrophobic. Therefore, during filtering of watery solutions, one needs a certain minimum pressure to overcome the capillary depression in the pores in order to be able to force water into and through the pores at all. The hydrophobic phenomenon as stated provides a quite undesired capillary depression which is of disadvantage in the process of watery solution. On the other hand, such a capillary depression may in other instances be quite desirable. For example, in the manufacture of textiles for making for example, waterproof clothing, canvas or the like, the problem arises that the material should be water-tight, but should still be permeable to air and water vapor in order to avoid impediment of transpiration. Textiles having these properties have in common with the membranes of the type mentioned above that generally they are to provide for a separation of substances and/or phases of matter. Therefore, it is quite reasonable to presuppose that technologies which are suitable and impart upon membranes these particular desired properties and conversely avoid the above-mentioned undesirable properties, can also be used for textile processing.

It is known that membranes may require particular chemical and/or physical properties. It is also known to impart upon the membranes these properties by surface modification, generally understood. For example, undesired absorption can be reduced, for example, through coating with carbon or through grafting of particular functional groups, such as sulfonate groups. The wettability of hydrophobic membranes will be improved, i.e., the requisite capillary depresssion is reduced and the requisite operating pressure is reduced in that prior to filtration a tensid is placed on the membrane. However, a hydrophilization thus achieved is only temporary in nature because the tensides adsorb only physically and do not bind chemically to the surface of the membrane. A permanent hydrophilization, however, is attainable through chemically grafted polar groups on the surface of the membrane.

Vacuum or wet-coating are other methods being used for surface treatment. However, vacuum methods are disadvantaged by the fact that they do not permit coating of the inner walls of pores. Wet-coating is usable in some instances, but because of solution and swelling problems, they are not suitable for all kinds of membrane. Moreover, a controlled coating of the inner walls of pores is made difficult by variations in the local concentration of the particular modifying reactants of the solution so that indeed the coating provided on the inner walls of the pores is very inhomogenous. In view of diffusion it is hardly possible to maintain a definite concentration of the reactants at boundaries. Moreover, solution media which tend to swell the membrane material were also observed to transpose the reaction from the surface into the interior, i.e., the surface near regions of the pore walls of the membrane.

Finally, it is known to modify a membrane surface with the use of a plasma, again in order to provide the membrane with desirable hydrophilic properties. These kinds of modification methods are indeed effective only on the outer surfaces of a membrane, but not in the interior surfaces of the pores. On the other hand, the pores, and particularly their inner walls materially influence the behavior and characteristics of the membrane, particularly as far as hydrophilic hydrophobic properties are concerned. Therefore, it is necessary to extend any kind of modification method into the interior pore surfaces of a membrane. In order to obtain this result, it is known to treat the membranes with chemically or biochemically active liquid substances which are forced through the pores. (See for example, German printed patent applications Nos. 2615815 and 2650921). These methods are of course wet-coating methods. However, the utilization is limited whenever the aforementioned disadvantages of the wet-coating method generally are encountered.

DESCRIPTION OF THE INVENTION

It is an object of the present invention to provide a neW and improved method for modifying the surface, particularly the surface portions of interior pore walls of objects such as membranes of the type mentioned above and to avoid the disadvantages outlined above with regard to the known vacuum and wet-coating method, but permits a controllable modification of the surface of the membrane as defined, including particularly the inner walls of the pores.

In accordance with the preferred embodiment of the present invention, it is suggested to activate the pore walls by means of a gas or a gas mixture or blend which in turn has been activated by partial electrical brush discharge. The term "partial brush discharge" is to refer to an electric discharge process which is largely equivalent to a regular brush discharge, but fills only a portion of a particular space such as a gas chamber in between the electrodes because at least one electrode will be surrounded by an insulating material.

In furtherance of this invention, it is suggested to provide a flow hyphen through chamber for reaction gas and to partition that chamber by means of the porous objects whose cell or pore walls are to be modified, there being accordingly an upstream and a downstream side and an electrode system is disposed upstream from the downstream side to obtain brush discharge in the gas not later than after having passed through the porous object, e.g., a membrane.

The gas or gas mixture to be activated is preferably composed of a carrier gas which is basically inert, at least as far as the present procedure is concerned, and of a reaction gas or a reaction gas mixture. However, a carrier gas may not necessarily be used so that the gas may be the reaction gas itself, or a blend of reaction gasses may be used. By way of example, a carrier gas to be used is preferably one of the noble gasses such as argon, neon, or helium. Reaction gasses are, for example and typically, sulfur dioxide, oxygen, carbon dioxide, nitrogen oxide, and acrylonitrile. These gasses upon being activated furnish certain functional groups as reaction products. For example, sulfur dioxide used as a reaction gas and when electrically activated, provides the sulfonate group $-SO_3^-$. Acrylonitrile, i.e., $CH_2CHCN$ when activated, provides the acrylonitrile group of like composition but

$-CH_2CHCN.$

Instead of a single reaction gas as stated, one can use a blend of several reaction gasses, which either provide similar types of reaction products or upon being activated then undergo reaction to obtain particularly compound reaction groups. For example, a blend of oxygen and carbon dioxide can be used. When activated they establish oxygen containing polar groups which are particularly useful for hydrophilization. If one uses hydrogen and nitrogen as reaction gas, then one can obtain the hydrophilizing groups $NH_4^\pm$ or $NH_3^-$.

It is a particular critical feature of the inventive method that the active groups which are produced through the discharge reaction in a gas or a gas mixture contain for example, $H_2S$ and $HNO_3$ for the production of $N_2$ and $2O_2$. These groups are generated through electric discharge process as described and will become chemically active at the inner walls of the pores in a membrane.

Particularly for hydrophilization, which is one of the most critical aspects of surface treatment within the purview of this invention, several materials have already been mentioned above, but many other polar ionogenic as well as nonionogenic groups can be generated. For example, a cabonyle compound will produce

a carboxyl compound will produce;

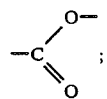

a hydroxyl compound will produce $-OH$; amino compounds will produce $-NH_2$ and in a watery medium, it will produce $-NH_4^+$; phosphorus oxychloryl compositions will produce $-OPCL_2$; sulphydryl compositions will produce $-SH$.

On the other hand, in other instances, hydrophobic properties may be desired, and in accordance with the invention, one may use here, for example, certain reaction gasses, such as low molecular fluoro carbon compounds such as $C_2F_4$. Also, at least to some extent, one can use alkane or alkene, for example, cyclohexene or siloxane.

In furtherance of the invention, it is desired to reduce interraction on the membrane with proteins and one wants to improve the biological compatability of the membrane. For this it is suggested to practice the inventive methods under utilization of negative inorganic groups, such as particularly, sulfonate $-SO_3^-$, phosphate $-PO_4^{--}$ or certain nonionogenic inorganic polar groups, such as nitrile $-NO_2$ and sulphydryl $-SH$. In the case of formation of networks, organic groups may be used such as acrylicnitril

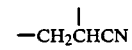
$-CH_2CHCN$

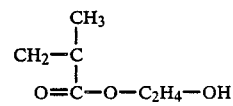

or hydroxyethylmethacryl

In accordance with a different aspect of the invention, antimicrobic groups or layers can be deposited on membranes, air permeable covers, air filters for extreme clean rooms, all in accordance with the method of this invention. For these instances, one will use preferably metals such as silver, copper, vanadium, titanium and so forth, which are provided by means of volatile or sublimable organic metal compounds. For example, titanium alkyle such as tetramethyl-titane or vanadiumcarbonyl is usable. Aside from metal or metal salts, other groups acting in an antimicrobic fashion can be used, for example, amino salts, quaternary ammonium salts or organo-silicon substituted organic amines. Another area in which the invention can be practiced concerns biotechnology requiring for example, to fix enzymes in cells on the membrane. In order to maintain the biochemical activity of the enzymes, it is frequently necessary to fix them through a molecular "spacer" onto the solid surface involved, being in this case the pore walls of the membrane. Such "spacer" may for example be alkylamine such as $-C_6H_{12}NH_2$. Such groups can indeed be placed onto the inner wall of the membrane by the method of the invention. The enzymes themselves are then affixed onto the molecular spacers separately and in a conventional manner.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

FIG. 2 is a view similar to FIG. 1 but showing a further modification;

FIG. 4 is another example of realizing the preferred embodiment with a more complex electrode structure; and FIG. 5 illustrates a further example for practicing the invention on a continuous basis.

Figure 1:
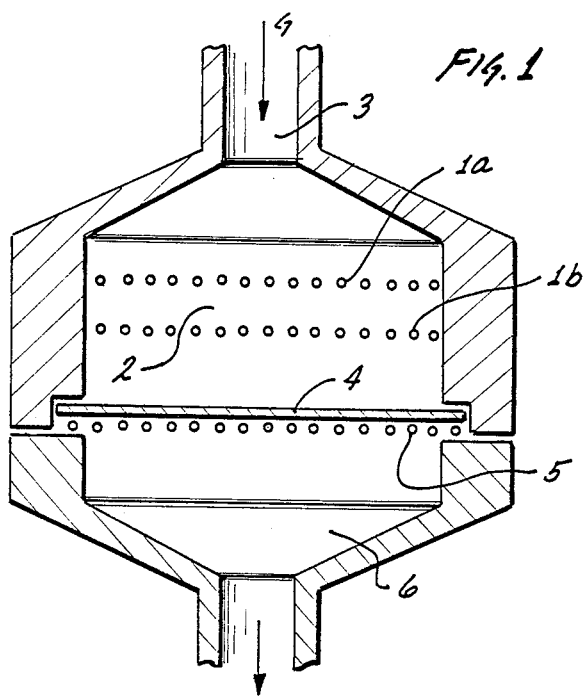
FIG. 1 is a schematic view through a first example, for practicing the preferred embodiment of the invention in accordance with a realization of the best mode.

Proceeding now to the detailed description of the drawing, reference is made first to FIG. 1. The Figure illustrates a feed pipe 3 by means of which a gas or a mixture of gas G is fed into a chamber 2 being so to speak, closed by a partition which is the membrane 4 to be processed. Reference numerals 1a and 1b refer to two sets of insulated electrodes or electrode systems through which partial brush discharges are maintained in the gas flow. The gas is basically forced through the membrane 4 from the upstream chamber 2 and into the downstream chamber 6, the membrane thus partitioning the chamber 2, 6. By providing the flow of gas through the inlet pipe 3 at the appropriate pressure which correspondingly pressurizes the pores in the membrane, the gas will flow through accordingly. Alternatively, the gas discharge or downstream chamber 6 of the arrangement may be subject to low pressure which is transmitted, so to speak, into the pores and the gas is now sucked through.

The activation of the gas is carried out through electrical, partial brush discharges between the electrodes and for this one provides an AC voltage at a comparatively high frequency such as one kilohertz or more up to several tens of megahertz. A frequency of ten kilohertz which is a medium frequency range or a frequency of 13.65 megahertz, which is a high frequency has been found practical. The voltage is selected from within the range of from 100 volts to 5 kilovolts, but preferably a range from 100 to 500 volts has been used.

Another parameter is the flow speed of the gas which, of course, is directly dependent upon the pressure gradient between upstream and downstream sides of the system with the pore diameter being a modifying factor. Another important operating parameter is the absolute (static) gas pressure as a measure of the free path length of the molecules. A further parameter is, of course, the particular gas composition.

Through selection of the gas dynamics, as well as the electrical parameters, one can possibly through trial and error find the optimum conditions as to uniformity and intensity of the treatment of the membrane, that is uniformity of the activating coating as well as its thickness. It is apparent that the gas pressure can be reduced for larger pores diameters. For example, in the case of a pore diameter of about 0.1 micrometer, the static pressure can be quite the normal atmospheric pressure, which of course, is independent from the pressure gradient that is needed to obtain directly the flow. If the pores of the membranes are smaller, for example, 10 nanometers, the static pressure should be increased up to about 8 bars. Conversely, if the pore diameters are relatively large, such as 1 micrometer, the static pressure should actually be below normal, for example, below $10^{-2}$ bars.

The immediate activation of the reaction gas in the pores of the membrane may be provided alternatively in a pulsating fashion, but in special cases there may be a continuous discharge into the pores. Pulsation, however, is preferred and it may be of advantage to provide pulses with a duration between 10 nanoseconds and 100 microseconds with a repetition frequency between 1 hertz and 10 kilohertz. The repetition frequency depends in the case of unipolarity upon the relaxation period necessary to permit a charge neutralization in the electrodes. The relaxation period depends in turn on the gas pressure and the dimensions of the pores as well as the conductivity of the surface of the membrane material. In the case of alternating voltage pulses higher frequencies can be considered as stated. Using generally short duration pulses is also beneficial for avoiding undesired heating of the membrane. Furthermore, the pulses are adapted to obtain a controlled transport of positive or negative charged molecules, i.e., ions, for example, more to the edge of a pore to provide a controlled and selective activation of the pore walls.

Figure 1A:
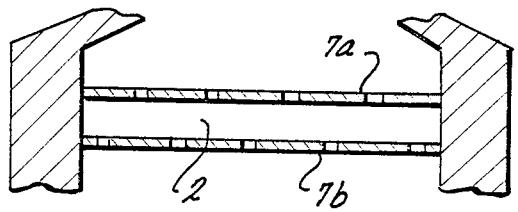
FIG. 1A illustrates an immediate modification of the device shown in FIG. 1 involving the electrical discharge structure.

The electrodes 1a and 1b are shown in FIG. 1 basically as wide meshes, nets or the like. However, both sets of electrodes are in the upstream chamber, well upstream from the membrane. The space between the electrodes is the electric-activating chamber proper. One or both electrodes, can be electrically insulated. The modification shown in FIG. 1a depicts the electrode 7a and 7b as disks with apertures. In any event, these electrodes are insulated in the sense that they are electrically isolated against contact with gaseous charge carriers. One does not want a spark discharge nor are corona discharges as narrowly understood desired.

This physical separation is not so much needed from a point of view of capture of gas material by the electrodes, but conversely it has to be avoided that the electrode material is to some extent separated (sparking off) from the electrodes and may thus be added to the gas flow. Such a side effect has to be prevented because such electrode particles would in fact contaminate the pore surfaces in the memrane to be modified. Moreover, the isolation as defined, has as its further goal that the electric power of the system is in fact capacitively coupled into the reaction chamber. This means, then, that the discharges occur with the gas itself and not at the electrodes. There will be no current flow through the gas chamber as between the electrodes. The electrodes are insulated through a synthetic or coating or synthetic film or through a synthetic hose over at least one of the electrode wires. Of course, both electrodes do not have to be insulated. One may use here, for example, a polyfluorocarbon, such as polytetrafluorolethylene, or polyolefine, polyester or polyethyleneterephtalate.

The types of electrodes illustrated in FIG. 1 and 1A do not constitute the only types of configurations for electrodes, but dependent upon the shape of the membrane, an object to be treated generally, different configurations can be used. Of course, in all instances, it is necessary that the flow of gas can pass through and one has to make sure that the entire gas flow, i.e., the entire flow of the gas which constitutes or includes a reaction component which is to be activated will pass through the electrical reaction chamber proper as defined between the respective sets of electrodes. Generally speaking, if the membranes are round, then the electrodes could be configured in terms of two co-axial rings which are either axially spaced or are situated in a single plane. One may use instead an aperture disk and a ring in co-axially related position thereto. One may also use a point type electrode being circumscribed by a co-axial ring. In the case of a rectangular type membrane, one will preferably use as electrodes parallel wires or rods. One may in many instances provide combinations of these configurations.

As far as the membrane 4 is concerned, it sits on a porous support 5 as schematically indicated, basically above the discharge or low pressure or suction side downstream chamber 6. In practice, a polycarbonate membrane was treated by means of such a structure and device. The membrane had a pore diameter of about 0.4 micrometers. Sulfur dioxide gas at a pressure of 1 bar on the feed and upstream side and 0.1 bars at the suction or downstream side was applied for 1 minute. The electrodes of the type illustrated were spaced by 5 millimeters and the voltage was 5 kilovolts at a frequency of 5 kilohertz. It was indeed observed that the membrane was hydrophilized by such a treatment.

In order to activate the interior walls of the pores more intensely, a configuration as shown in FIG. 2 can be used. Here, the insulated electrodes are provided as gas permeable areal electrodes 8a and 8b which are respectively arranged to both sides of the membrane 4 and more or less tightly connected to the surface of the membrane. Thus, the electrical activation as it affects the gas occurs still before the gas reaches the downstream side. An energization voltage is applied through conductors 10. The activation occurs in this case as the gas flows through the pores. In this case, then, electrode 8b may serve also as a support for the membrane. The activation, therefore, occurs in this case as the gas flows through the pores. For the same purpose and in lieu of the insulated electrodes, one may provide an arrangement of point or edge-like electrodes at least one of which being electrically insulated and being configured and positioned to force a brush like discharge through the pores. In this case, then, one will surface activate also the pore walls directly through the discharge process.

Figure 3:
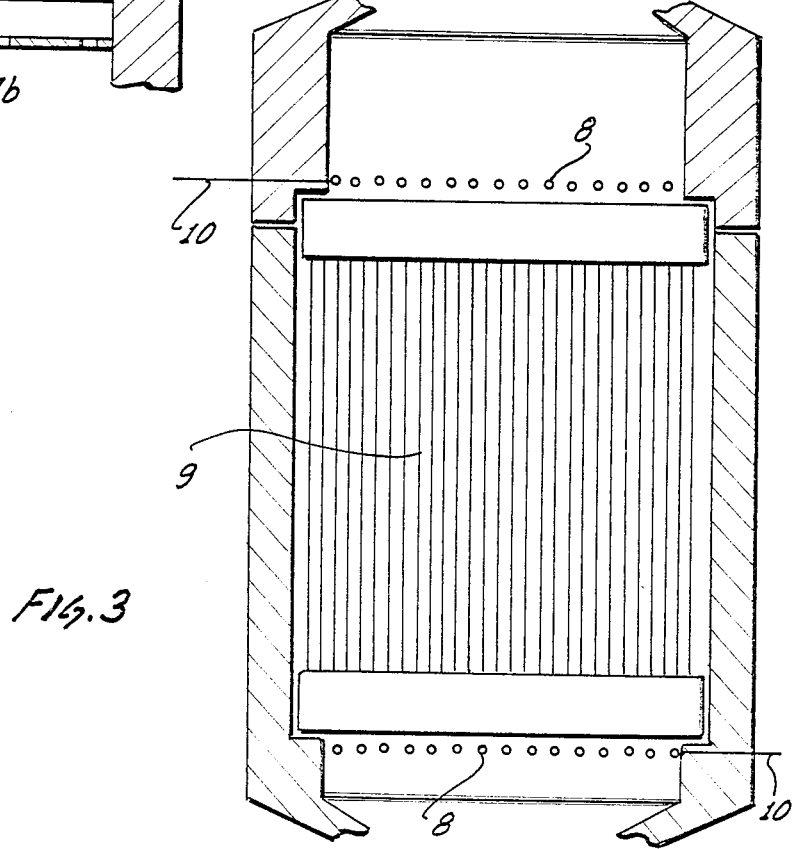
FIG. 3 illustrates a modification of the structure shown in FIG. 2 for practicing the invention with a thicker porous object.

The basic electrical configuration as per FIG. 2 is also suitable for modifying the surfaces of hollow fiber object 9 to be used in a hollow fiber module. This is illustrated by way of example in FIG. 3. Thus, the hollow fiber module 9 is in this case the "membrane" and differs from the usual membrane only through the thickness dimension, but the aspects of importance here are the same: activation of interior wall surfaces. The electrodes 8 in this case are also configured to sandwich the module 9 in between and they abut accordingly the front faces of the hollow fiber module.

Proceeding now to the description of FIG. 4, there is illustrated a different embodiment and example for practicing the invention, but serving also for intensifying the activation of the pore walls of the membrane 4. In this case, one provides two net or mesh like electrodes 1a and 1b to one side of the membrane 4, while a third likewise gas permeable counter electrode 11 is provided on the other side of the membrane and again it may serve as a kind of membrane support. Depending upon the membrane, these electrodes can have any of the configurations mentioned earlier. In this case, then, the upper electrode 1b on the membrane 4 cooperates with the two other electrodes, the upstream electrode 1a and the electrode 11. This way one obtains, so to speak, a preactivation of the gas as it flows towards the membrane 4 and further activation possibly also an activation of the pore walls themselves is obtained through the electrode configuration and arrangement as it resembles FIG. 2.

The example shown particularly in FIGS. 1, 2, 3 and 4, show individual objects such as membranes, etc. to be treated and processed inidividually, so to speak, one at a time. However, one can understand these Figures also as a cross-section through a chamber, which in a direction perpendicular to the drawing, has narrow and sealed openings through which a membrane, sheet or strip can be passed in a continuous fashion so that this membrane sheet is treated in a continuous process.

FIG. 5 illustrates a further modification for obtaining a continuous treatment process. In this case, the membrane 40 is a sheet or a strip which runs along a curved path. i.e., in a cylindrical surface established as a curved track in the following manner. One can consider a first set of annularly distributed electrodes 12 to define a cylinder or drum, the electrodes being of a mesh or sieve like construction with appropriate insulation. The membrane sheet 40 is caused to run over that cylinder. In realization, for example, of the electrode arrangement shown in FIG. 2, a second similarly constructed gas permeable electrode 14 delineates, so to speak, the outer portion of this cylindrical track on which the membrane 40 runs.

The interior of this drum like arrangement is partitioned into sectors 15. The drum has a hub 19 and a valve therein connects to a tube 13 basically in order to establish a vacuum in these sectors 15. Thus, gas is sucked radially inwardly through the membrane sheet as it progresses on its path. The gas flow G is divided through a manifold system 16 to be forced through the gas permeable electrode 14, and by suction through the membrane 40 as described. An appropriate alternating voltage is applied between the electrodes 12 and 14 to activate the gas as it penetrates into and flows through the pores of the membrane 40. The sectors 17 of the interior of the drum arrangement are not juxtaposed to portions of the membrane 40 so that pumping is not applied thereat. Reference numeral 18 refers to two guide sheaves or pulleys to guide the membrane 40 into and out of the drum arrangement.

The invention is not limited to the embodiments described above; but all changes and modifications thereof, not constituting departures from the spirit and scope of the invention are intended to be included.

We claim:

1. A method for modifying the surface of the pore walls of a mebrane made of an organic compound material and to be used for separating materials and/or phases of matter comprising the steps of:

providing a flow of gas and forcing said gas through said membrane, said gas comprising or including at least one particular reaction medium, for electrochemically activating the membrane; and providing partial electrical brush discharge through said gas, at a point in time prior to the gas having passed through said membrane, for electrically activating said particular reaction medium so that said then activated reaction medium in turn modifies and chemically activates the surface of said pore walls.

2. Method as in claim 1, said gas including an inert carrier gas selected from a group consisting of a noble gas, argon, neon or helium and at least one reaction gas serving as the reaction medium.

3. Method as in claim 1, said gas including at least two reaction gasses which upon being electrically activated by said discharge, react with each other so that a resulting reaction production in turn activates said pore walls.

4. Method as in claim 1, wherein said discharge is carried out through alternating voltages with a frequency in the range from 1 kilohertz up to the megahertz range at a voltage between 10 volts to 5 kilovolts.

5. Method as in claim 1, said discharge being carried out through pulses with a pulse duration between 10 nanoseconds and 100 microseconds at a repetition frequency between 0.1 hertz and 10 kilohertz.

6. A method for treating the interior surface of pores in a porous object comprising the steps of providing a gas which includes at least one particular reaction gas for chemically activating the surfaces of the pores
    forcing said gas through the pores of said object; and
    providing a pulsating or alternating electrical discharge of partial brush discharge nature under utilization of electrodes being electrically insulated in relation to each other, the discharge to occur in said gas at a point in time prior to the gas having been forced completely through said porous object such that reaction ions developed in said gas on account of the electrical discharge will chemically bond as reaction product to inside surface of the pores of the material of the object.

7. Method as in claim 6 and including the step of obtaining a partial brush discharge on the object itself for activating the pore walls of the object directly.

8. Method as in claim 6, wherein said object is rendered bio-compatible by the reaction.

9. Method as in claim 6, wherein said object is a membrane to be used for filtering of biological fluid.

10. Method as in claim 6 wherein said object is an air filter.

11. Method as in claim 6 wherein said reaction product as deposited on the pore walls becomes a molecular spacer, the object being a biochemically active membrane, the spacer molecules provided for carrying enzymes.

12. Method as in claim 6 wherein said object is air permeable waterproof textile material.

13. Method as in claim 6 wherein said object is a membrane, said reaction product hydrophilizing the membrane.

14. Method as in claim 8 wherein said object is a membrane, said reaction product hydrophobizing the membrane.

* * * * *